United States Patent
Kosel et al.

(10) Patent No.: US 12,360,606 B2
(45) Date of Patent: Jul. 15, 2025

(54) CONTROLLING DEVICES USING FACIAL MOVEMENTS

(71) Applicant: KING ABDULLAH UNIVERSITY OF SCIENCE AND TECHNOLOGY, Thuwal (SA)

(72) Inventors: Jürgen Kosel, Thuwal (SA); Abdullah Saud Almansouri, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 233 days.

(21) Appl. No.: 17/631,937

(22) PCT Filed: Jul. 31, 2020

(86) PCT No.: PCT/IB2020/057279
§ 371 (c)(1),
(2) Date: Feb. 1, 2022

(87) PCT Pub. No.: WO2021/024138
PCT Pub. Date: Feb. 11, 2021

(65) Prior Publication Data
US 2023/0144759 A1    May 11, 2023

Related U.S. Application Data

(60) Provisional application No. 62/882,006, filed on Aug. 2, 2019.

(51) Int. Cl.
G06F 3/01 (2006.01)
A61F 4/00 (2006.01)
(Continued)

(52) U.S. Cl.
CPC .......... *G06F 3/017* (2013.01); *A61F 4/00* (2013.01); *A61G 5/04* (2013.01); *G05D 1/0016* (2013.01);
(Continued)

(58) Field of Classification Search
CPC ........... A61G 2203/30; A61G 2203/36; A61G 2203/18; A61G 5/04; A61G 5/1051;
(Continued)

(56) References Cited

U.S. PATENT DOCUMENTS

| 4,838,347 A | * | 6/1989 | Dentini | H05K 7/20545 |
| | | | | 439/91 |
| 5,363,858 A | * | 11/1994 | Farwell | A61B 5/377 |
| | | | | 607/139 |

(Continued)

FOREIGN PATENT DOCUMENTS

| CN | 104331160 A | 2/2015 |
| CN | 108272566 A | 7/2018 |

(Continued)

OTHER PUBLICATIONS

Coordination of Orofacial Motor Actions into Exploratory Behavior by Rat (Year: 2017).*

(Continued)

*Primary Examiner* — Fadey S. Jabr
*Assistant Examiner* — Faris Asim Shaikh
(74) *Attorney, Agent, or Firm* — PATENT PORTFOLIO BUILDERS PLLC

(57) ABSTRACT

A system for controlling at least one device includes a pair of glasses having a glasses frame. A plurality of magnetic sensors, a processor coupled to the plurality of magnetic sensors, and a wireless communication transmitter coupled to the processor are arranged on or in the glasses frame. A plurality of magnetic skins tags are arranged on a human (Continued)

face. The plurality of magnetic sensors sense movement of at least one of the plurality of magnetic skin tags and transmit a signal corresponding to the sensed movement to the processor. The processor, responsive to receipt of the signal corresponding to the sensed movement, transmits a signal for controlling the at least one device via the wireless communication transmitter to a processor of a power-driven mobility device.

20 Claims, 7 Drawing Sheets

(51) Int. Cl.
*A61G 5/04* (2013.01)
*G05D 1/00* (2024.01)

(52) U.S. Cl.
CPC .......... *G06F 3/012* (2013.01); *A61G 2203/18* (2013.01); *A61G 2203/30* (2013.01)

(58) Field of Classification Search
CPC ............ A61F 4/00; G06F 3/012; G06F 3/017; G06F 2203/0383; G06F 2203/0384; G05D 1/0016; G05D 2201/0213; G05D 2201/02; G05D 2201/0206; G05D 2201/0209; G05D 2201/0207; G05D 2201/0218; G05D 1/02; G05D 1/0259; G05D 3/00; G02C 2200/02; G02C 11/10; G01D 2205/40; G01D 2205/70; G01D 2205/90; G01D 2205/95; G01D 2205/73; A61B 5/112; A61B 5/1127; A61B 5/1126; A61B 5/1103; H01F 1/00
See application file for complete search history.

(56) References Cited

U.S. PATENT DOCUMENTS

| | | | | |
|---|---|---|---|---|
| 5,748,113 | A * | 5/1998 | Torch | A61B 5/1103 341/20 |
| 11,730,645 | B1 * | 8/2023 | Dean | A61G 5/10 701/24 |
| 2001/0028309 | A1 * | 10/2001 | Torch | A61B 5/1103 340/576 |
| 2007/0100511 | A1 * | 5/2007 | Koerlin | A61F 4/00 701/1 |
| 2008/0092443 | A1 * | 4/2008 | Herman | E05F 15/77 49/25 |
| 2009/0309747 | A1 | 12/2009 | Ghovanloo et al. | |
| 2012/0281181 | A1 * | 11/2012 | Chen | G02B 30/35 351/159.76 |
| 2012/0316884 | A1 * | 12/2012 | Rozaieski | A61G 5/10 704/E21.001 |
| 2013/0090931 | A1 * | 4/2013 | Ghovanloo | A61F 4/00 704/275 |
| 2015/0302854 | A1 * | 10/2015 | Clough | G16H 40/67 704/275 |
| 2016/0296391 | A1 * | 10/2016 | Soklaski | A61G 3/062 |
| 2017/0189250 | A1 * | 7/2017 | Juhasz | B60L 15/20 |
| 2018/0147099 | A1 * | 5/2018 | Jones | A61B 5/389 |
| 2019/0142349 | A1 * | 5/2019 | Schorey | A61B 5/11 600/546 |
| 2019/0350482 | A1 * | 11/2019 | Jones | B60L 15/00 |
| 2020/0195463 | A1 * | 6/2020 | Johnson | G06V 40/176 |
| 2021/0137455 | A1 * | 5/2021 | Connor | A61B 5/6803 |

FOREIGN PATENT DOCUMENTS

| | | | | |
|---|---|---|---|---|
| CN | 110353899 B | * | 11/2020 | ......... A61B 5/0496 |
| JP | 2005091203 A | * | 4/2005 | |
| WO | WO-2018090109 A1 | * | 5/2018 | ............. A61F 4/00 |
| WO | WO-2019127368 A1 | * | 7/2019 | ............. A61G 5/04 |
| WO | 2020144598 A2 | | 7/2020 | |

OTHER PUBLICATIONS

Translation of JP-2005091203-A retrieved from Espacenet on Jan. 25, 2024 (Year: 2024).*
Translation of CN-110353899-B retrieved from Espacenet on Jan. 25, 2024 (Year: 2024).*
Magnetorheological Elastomers: Materials and Applications (Year: 2019).*
Recent Progress on Magnetorheological Solids: Materials, Fabrication, Testing, and Applications (Year: 2014).*
Cerebral Palsy EEG Signals Classification: Facial Expressions and Thoughts for Driving an Intelligent Wheelchair (Year: 2012).*
Augmenting a voice and facial expression control of a robotic wheelchair with assistive navigation (Year: 2014).*
A Wheelchair Control System Using Human-Machine Interaction: Single-Modal and Multimodal Approaches (Year: 2017).*
A facial expression controlled wheelchair for people with disabilities (Yearh: 2018).*
Translation of WO-2018090109-A1 retrieved from Espacenet on Apr. 4, 2025 (Year: 2025).*
Translation of WO-2019127368-A1 retrieved from Espacenet on Apr. 4, 2025 (Year: 2025).*
Huo, X., et al., "A Wireless tongue-Computer Interface Using Stereo Differential Magnetic Field Measurement," Proceedings of the 29th Annual International Conference of the IEEE EMBS, Cite International, Lyon, France, Aug. 23-26, 2007, pp. 5723-5726, IEEE.
International Search Report in corresponding/related International Application No. PCT/IB2020/057279, date of mailing Dec. 21, 2020.
Written Opinion of the International Searching Authority in corresponding/related International Application No. PCT/IB2020/057279, date of mailing Dec. 21, 2020.

* cited by examiner

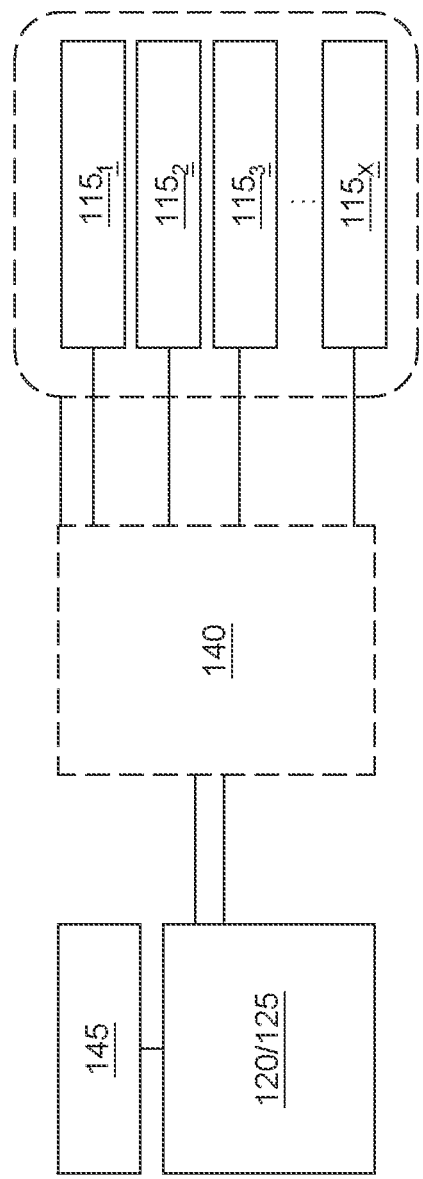

CONTROLLING DEVICES USING FACIAL MOVEMENTS

CROSS-REFERENCE TO RELATED APPLICATIONS

This application is a U.S. National Stage of International Application No. PCT/IB2020/057279, filed on Jul. 31, 2020, which claims priority to U.S. Provisional Patent Application No. 62/882,006, filed on Aug. 2, 2019, entitled "METHOD FOR FACIAL EXPRESSION TRACKING," the disclosures of which are incorporated herein by reference in their entirety.

BACKGROUND

Technical Field

Embodiments of the disclosed subject matter generally relate to systems and methods for controlling devices, including power-driven mobility devices and devices other than power-driven mobility devices, using facial movements.

Discussion of the Background

Quadriplegia is a condition in which a person does not have the ability to control their arms and legs, which makes it difficult for people with this condition to live independently. These types of injuries typically occur to middle-age adults, who accordingly require lifetime solutions to allow them to interact with the world.

Due to the loss of ability to control their arms and legs, quadriplegics cannot use conventional assistive technology (i.e., power-wheel chairs operated using a joystick) to move around. Various solutions have been proposed to address this issue, including spin-n-puff, head or chin joysticks, brain-machine interfaces using neural detectors to interpret action commands, camera-based systems for facial and gaze detection, voice control, and tongue detection. These solutions, however, offer limited action commands, require bulky and invasive equipment (e.g., bulky transducers attached to sensitive organs), are expensive, or require significant computational power. Some of these solutions also require continuous attention by the patient to prevent the patient from moving and talking at the same time.

Some quadriplegics have more severe injuries (i.e., C1 and C2 injuries), and suffer from difficulty speaking, as well as difficulty moving their head and neck. For these people, the only remaining solutions are using cameras, tongue control, or neural detectors. These technologies have so far been implemented with very limited action commands. Specifically, the action commands are limited to those for controlling the power-driven mobility device itself. These solutions thus do not provide any ability to control devices other than the power-driven mobility device itself, and accordingly these solutions fail to provide quadriplegics with tools for living independently.

WO 2020/144598 discloses a system with magnetic skin tags and magnetic sensors that determine changes in magnetic fields generated by the magnetic skin tags. There is no discussion of how to use the system to address issues particular to quadriplegics.

Accordingly, there is a need for a solution for quadriplegics to control movement of a power-driven mobility device, as well as controlling devices other than power-driven mobility devices, without incurring high costs, requiring large computational power, and bulky and invasive equipment.

SUMMARY

According to an embodiment, there is a system for controlling at least one device. The system includes a pair of glasses comprising a glasses frame. A plurality of magnetic sensors, a processor coupled to the plurality of magnetic sensors, and a wireless communication transmitter coupled to the processor are arranged on or in the glasses frame. A plurality of magnetic skins tags are arranged on a human face. The plurality of magnetic sensors sense movement of at least one of the plurality of magnetic skin tags and transmit a signal corresponding to the sensed movement to the processor. The processor, responsive to receipt of the signal corresponding to the sensed movement, transmits a signal for controlling the at least one device via the wireless communication transmitter to a processor of a power-driven mobility device.

According to an embodiment, there is a method for controlling at least one device. At least one of a plurality of magnetic sensors arranged on a glasses frame sense a change in a magnetic field due to movement of at least one of a plurality of magnetic skin tags arranged on a human face. A wireless communication transmitter, coupled to or arranged in the glasses frame, transmits a signal corresponding to the sensed change in the magnetic field to a processor of a power-driven mobility device via a wireless communication transceiver of the power-driven mobility device. The processor of the power-driven mobility device determines a command corresponding to the signal. The processor of the power-driven mobility device controls the device based on the determined command.

According to an embodiment, there is a system for controlling a power-driven mobility device and at least one device. The system includes a pair of glasses comprising a glasses frame, a plurality of magnetic sensors, a processor coupled to the plurality of magnetic sensors, and a wireless communication transmitter coupled to the processor. A plurality of magnetic skins tags are arranged on a human face. The plurality of magnetic sensors are configured to sense movement of at least one of the plurality of magnetic skin tags and transmit a signal corresponding to the sensed movement to the processor. The system also includes a power-driven mobility device comprising a motor, a processor, an interface coupled to the processor and motor, a wireless communication transceiver coupled to the processor, and a wireless communication transmitter coupled to the processor. The processor of the pair of glasses, responsive to receipt of the signal corresponding to the sensed movement, transmits a signal for controlling the power-driven mobility device or the at least one device to the processor of a power-driven mobility device. The at least one device comprises a wireless receiver configured to wirelessly communicate with the wireless communication transmitter of the power-driven mobility device.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 1C is a schematic illustration of circuitry of a pair of glasses according to embodiments;

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of assistive technology.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1A:
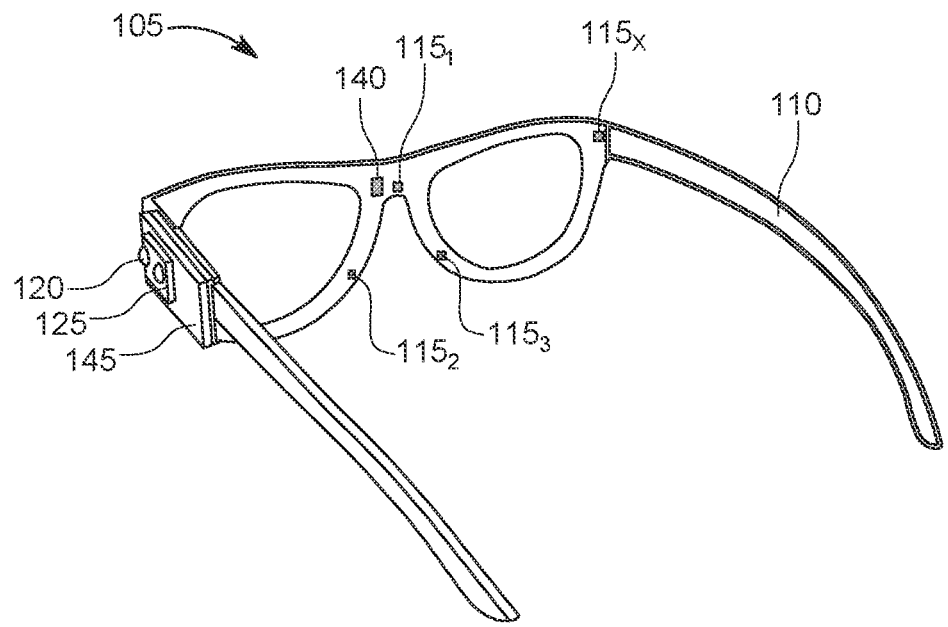
FIG. 1A is a schematic diagram of a pair of glasses according to embodiments.
Figure 1B:
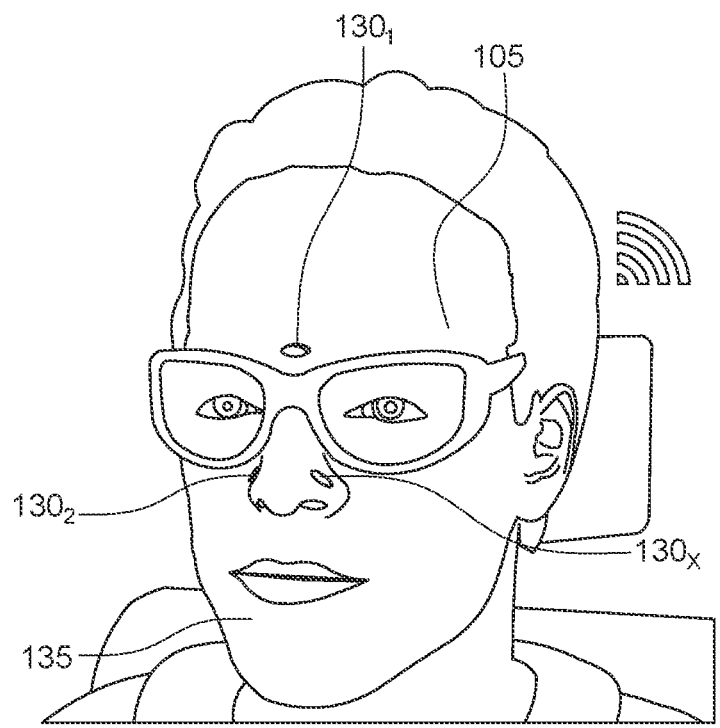
FIG. 1B is an illustration of a pair of glasses and magnetic skin tags on a human face according to embodiments.
Figure 2A:
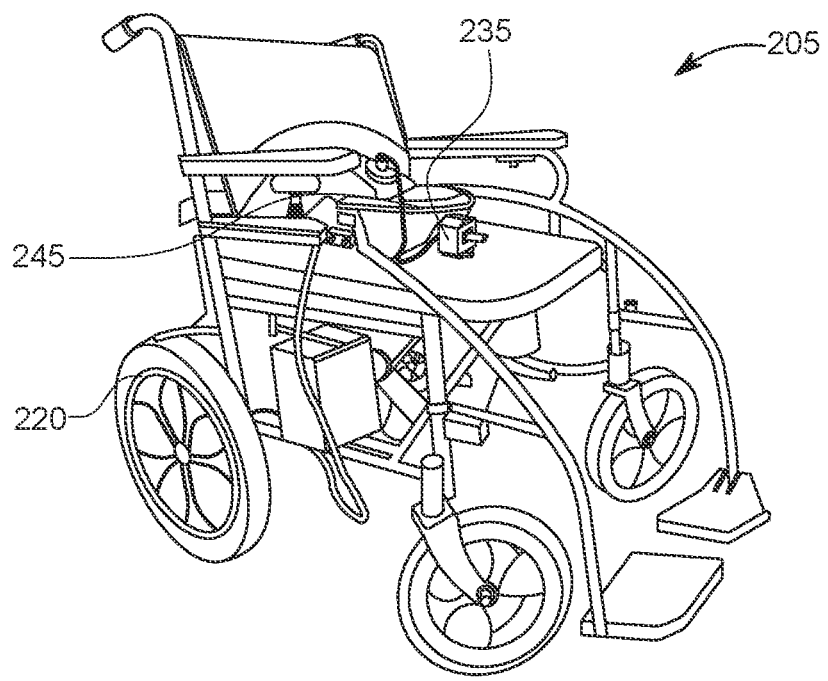
FIG. 2A is a schematic diagram of a power-driven mobility device according to embodiments.
Figure 2B:
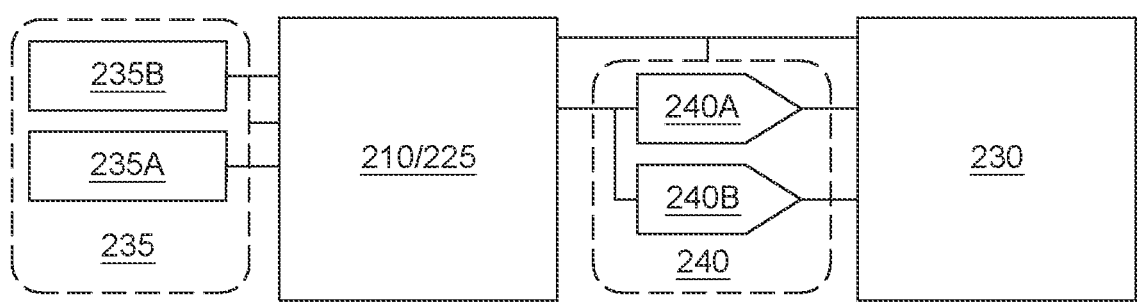
FIG. 2B is a schematic diagram of circuitry of a power-driven mobility device according to embodiments.
Figure 3:
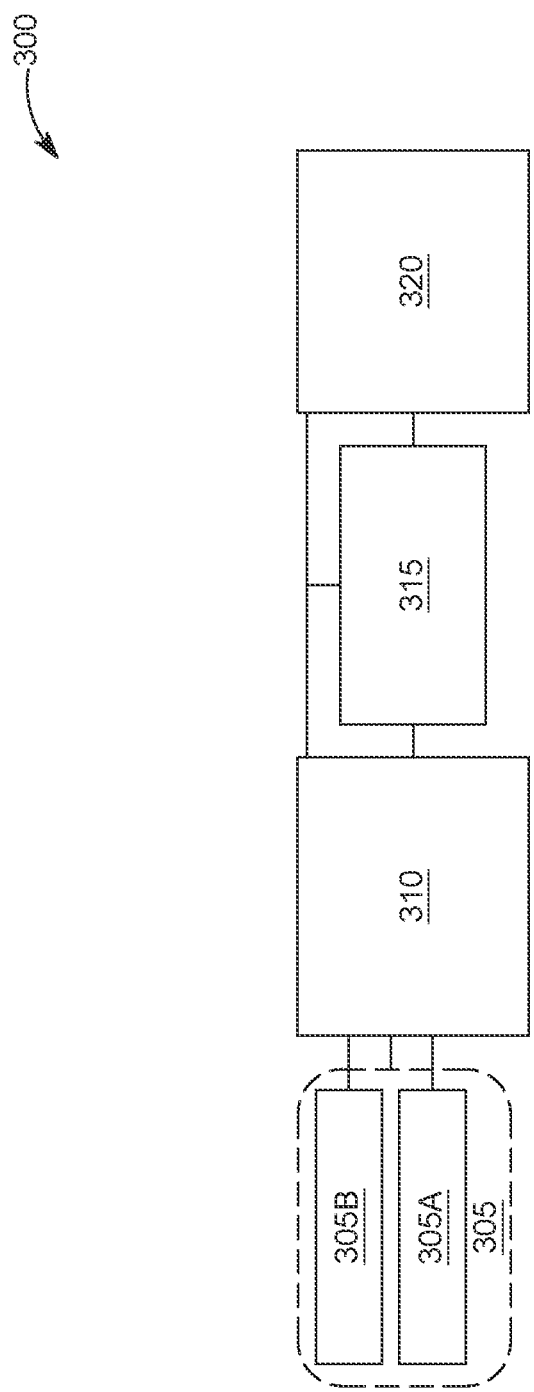
FIG. 3 is a schematic diagram of a system for controlling a device according to embodiments.

A system for controlling at least one device will now be described in connection with FIGS. 1-3, where FIGS. 1A-1C illustrate components worn on a human face, FIGS. 2A and 2B illustrate a power-driven mobility device, and FIG. 3 illustrates a device other than a power-driven mobility device that can be controlled by facial movements (the device of FIG. 3 is also referred to herein as the controlled device and the further device). The system includes a pair of glasses 105, which comprises a glasses frame 110. A plurality of magnetic sensors $115_1$-$115_x$, a processor 120 coupled to the plurality of magnetic sensors $115_1$-$115_x$, and a wireless communication transmitter 125 coupled to the processor 120 are arranged on or in the glasses frame 110. As illustrated in FIG. 1B, a plurality of magnetic skins tags $130_1$-$130_x$ are arranged on a human face 135. The plurality of magnetic sensors $115_1$-$115_x$ sense movement of at least one of the plurality of magnetic skin tags $130_1$-$130_x$ and transmit a signal corresponding to the sensed movement to the processor 120. The processor 120, responsive to receipt of the signal corresponding to the sensed movement, transmits a signal for controlling the at least one device 205 or 300 via the wireless communication transmitter 125 to a processor 210 of a power-driven mobility device 205. In embodiments, the wireless communication transmitter 125 can be a wireless communication transceiver capable of transmitting and receiving wireless signals.

The plurality of magnetic skin tags $130_1$-$130_x$ can be colored to match a user's skin tone, can be colored to be easily visible and identifiable, or can be colored in a manner that would be considered fashionable by the user. The plurality of magnetic skin tags $130_1$-$130_x$ can be secured to the face using any technique, such as using a bio-compatible adhesive (e.g., an adhesive that allows the underlying skin to breathe), a petroleum jelly, or any other substance that can secure the plurality of magnetic skin tags $130_1$-$130_x$ to a human face that will not irritate the user's skins when worn over a long period of time, such as hours, days, or weeks. Although FIG. 1B illustrates the plurality of magnetic skin tags $130_1$-$130_x$ as exhibiting an oval shape, the plurality of magnetic skin tags $130_1$-$130_x$ can have any shape, and in some implementations can be designed to spell out words, numbers of letters. In other words, the actual shape of the plurality of magnetic skin tags $130_1$-$130_x$ is immaterial so long as the plurality of magnetic skin tags $130_1$-$130_x$ produce a sufficient magnetic field, the change of which can be sensed by the plurality of magnetic sensors $115_1$-$115_x$.

Further, although FIGS. 1A and 1B respectively illustrate a particular arrangement of the magnetic sensors $115_1$-$115_x$ and the magnetic skin tags $130_1$-$130_x$, other arrangements are possible. In the other arrangements, there should be at least a 1-1 relationship between the number of magnetic sensors $115_1$-$115_x$ and the number of magnetic skin tags $130_1$-$130_x$ (e.g., there can be more than one magnetic sensor to sense changes in magnetic fields of one magnetic skin tag). Additionally, although FIGS. 1A and 1B respectively illustrate three magnetic sensors $115_1$-$115_x$ and three magnetic skin tags $130_1$-$130_x$ a greater number or fewer number of magnetic sensors and magnetic skin tags can be employed. Fewer magnetic sensors and magnetic skin tags reduces the number of possible commands and more magnetic sensors and magnetic skin tags increase the number of available commands. Accordingly, the location and number of magnetic skin tags and magnetic sensors can be customized to the needs of the user. For example, if the user does not have much control over his/her nose, then only the forehead magnetic skin tag and a corresponding magnetic sensor can be employed, or alternatively another location on the user's face can be used for the magnetic skin tags that are illustrated as being placed on the user's nose.

Referring specifically to FIGS. 1A and 1C, the processor 120 and wireless communication transmitter 125 can be part of the same component or can be separate components. A non-limiting example of a combined processor 120 and wireless communication transmitter 125 is a Bluno Nano chip, which is an Arduino Nano chip with Bluetooth 4.0 functionality. The glasses 105 also include a power source 145, such as a battery. Alternatively, or additionally, the power source 145 can be any other type of power source, such as a fuel cell, solar panel, etc. Although FIG. 1A illustrates the processor 120, wireless communication transceiver 125, and power source 145 being attached to the frame 110, these components can be integrated into the frame 110.

As illustrated in FIG. 1C, the plurality of magnetic sensors $115_1$-$115_x$ can be coupled to the processor 120 via a multiplexer 140 and provides measurements of changes in magnetic field in the form of a voltage that corresponds to the magnitude of the change in magnetic field. In a non-limiting example, the multiplexer 140 can be, for example, a PCA9548 octal bidirectional translating switch. It should be recognized, however, that, depending on the processor 120 employed, the multiplexer 140 can be omitted. In the illustrated embodiment, the upper line between the multiplexer 140 and the processor 120/wireless communication transmitter 125 is a data line (e.g., an SCL/SDA line) and the lower line is a power line for conveying power from the battery 145 to the multiplexer 140. Further, the upper line between the magnetic sensors $115_1$-$115_x$ is a power line for conveying power from the battery 145 to the magnetic sensors $115_1$-$115_x$ and the remaining lines are data lines (e.g., SCL/SDA lines). In one embodiment, the magnetic sensors are BM1422AGMV 3-axis digital magnetometers, which as discussed in more detail below, are configured to sense changes in magnetic field in only one of the three axes. However, other types of magnetic sensors can be employed. Further, the magnetic sensors $115_1$-$115_x$, such as the BM1422AGMV 3-axis digital magnetometers, can be configured to sense changes in magnetic fields in two or all three axes.

Referring now to FIGS. 2A and 2B, the power-driven mobility device 205 includes a motor (not visible in the figures) operatively coupled to at least one wheel 220 of the power-driven mobility device 205 to control movement of the power-driven mobility device 205. Although FIG. 2A illustrates a wheelchair as the power-driven mobility device, the disclosed embodiments can be employed with other types of power-driven mobility devices, such as electric scooters, golf carts, Segways®, and the like. Thus, consistent with the usage in the art, the term power-driven mobility device should be understood as any mobility device powered by batteries, fuel, or other engines that is used by individuals with mobility disabilities for purposes of locomotion.

As will be recognized by those skilled in the art, a power-driven mobility device can include a single motor coupled to two or more wheels or a separate motor for each wheel, and in many commercial wheelchairs (as well as electric scooters), motors are coupled to either the front or rear set of wheels (typically the motor is coupled to the larger of the front and rear set of wheels). The power-driven mobility device 205 also includes a wireless communication transceiver 225 coupled to the processor 210. An interface 230 is coupled to the processor 210 and motor. The processor 210 is configured to control movement of the power-driven mobility device 205 using interface 230 based on the signal for controlling the device transmitted from the pair of glasses 105 to the wireless communication transceiver 235 of the power-driven mobility device 205. In one embodiment, which can be used to retrofit an existing power-driven mobility device, the interface 230 is coupled to the controller of the power-driven mobility device's motor. In another embodiment, which can be used for a power-driven mobility device manufactured with the disclosed equipment, the interface is also the controller of the power-driven mobility device's motor.

Referring now to FIG. 2B, the components of the power-driven mobility device 205 include the processor 210 and wireless communication transceiver 225, which are coupled between a further wireless communication transceiver 235 and digital-to-analog converters 240. In an embodiment, wireless communication transceiver 225 of the power-driven mobility device 205 communicates with the wireless communication transmitter 125 of the pair of glasses 105 using radio frequencies and the power-driven mobility device 205 communicates with a further device 300 (see FIG. 3) using line-of-sight communications, such as using visible, near-infrared, or infrared frequencies. If the processor 210 includes digital-to-analog conversion circuitry, the digital-to-analog converters 240 can be omitted. In the illustrated embodiment, the wireless communication transceiver 235 can include a transmitter 235A and a receiver 235B.

In one non-limiting implementation, the further wireless communication transceiver can communicate using infrared frequencies in the 38 KHz frequency band. In the embodiment illustrated in FIG. 2B, the upper line is a data line to the receiver 235B, the lower line is a data line to the transmitter 235A and the middle line is a power line. Similar to the circuitry of the glasses 105, the processor 210 and wireless communication transceiver 225 can be part of the same component or can be separate components, and in a combined implementation a Bluno Nano chip can perform the required functionality of the two components. In the illustrated embodiment, the digital-to-analog converter 240 includes one analog-to-digital converter 240A for providing commands for controlling forward and backward movement (corresponding to forward and backward movement of the joystick on the power-driven mobility device) and a second analog-to-digital converter 240B for providing commands for controlling left and right movement (corresponding to left and right movement of the joystick on the power-driven mobility device). Depending upon implementation, a single analog-to-digital converter can be employed.

FIG. 3 is a schematic diagram of a system for controlling a device according to embodiments. This controlled device (also referred to herein as the further device) is a device other than the power-driven mobility device, including, but not limited to, a light, a door, a window, an elevator, a television, a set-top box, a pedestrian traffic light, a phone, curtains, doors, or a computer. In other words, the controlled device can be any device requiring physical actions/manipulation that cannot be performed by quadriplegics but can be performed by persons without quadriplegia. The controlled device includes a wireless communication receiver 305 coupled to a processor 310. Similar to the wireless communication transceiver 225, the wireless communication receiver 305 can be a transceiver that includes a transmitter 305A and a receiver 305B, and can communicate, for example, using line-of-sight communications with infrared frequencies, such as the 38 KHz band. However, other frequencies and line-of-sight communication technologies can be used, as desired. Processor 310 is coupled to an interface 315 to the controlled device 320. The interface 315 can include, for example, a digital-to-analog converter, relay, etc. for converting control signals from processor 310 into a format suitable for controlled device 320. Alternatively, the controlled device 320 can be manufactured to operate with the system, in which case the transceiver and processor of the controlled device 320 itself can be configured in the manner described herein to control the controlled device 320.

In the embodiment illustrated in FIG. 3, the upper line between the wireless communication receiver 305 and processor 310 is a data line to the receiver 305B, the lower line is a data line to the transmitter 305A, and the middle line is a power line. Further, the processor 310 provides power to both the interface 315 and the controlled device 320 using the upper line in FIG. 3. The lower line between the processor 310 and the interface 315 provides data commands from processor 310 to interface 315, and the lower line between the interface 315 and the controlled device 320 provides data commands from the interface 315 to the controlled device 320.

Figure 4A:
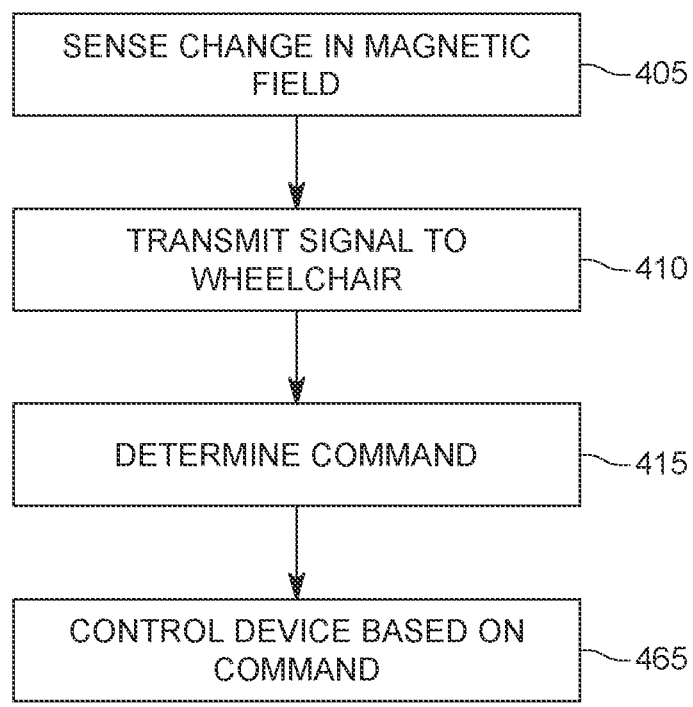
FIGS. 4A and 4B are flowcharts of a method for controlling at least one device according to embodiments.

A method for controlling at least one device 205 and/or 300 will now be described in connection with FIG. 4A. At least one of a plurality of magnetic sensors $115_1$-$115_x$ arranged on a glasses frame 110 senses a change in a magnetic field due to movement of at least one of a plurality of magnetic skin tags $130_1$-$130_x$ arranged on a human face 135 (step 405). The changes in magnetic field are conveyed by the plurality of magnetic skin tags $130_1$-$130_x$ in the form of a voltage having a magnitude corresponding to the magnitude of the change in the magnetic field. A wireless communication transmitter 125 coupled to or arranged in the glasses frame 110 transmits a signal corresponding to the sensed change in the magnetic field to a processor 210 of a power-driven mobility device 205 via a wireless communication transceiver 225 of the power-driven mobility device 205 (step 410). The processor 210 of the power-driven mobility device 205 determines a command corresponding to the signal (step 415). The processor 210 of the power-driven mobility device 205 controls the device 205 and/or 300 based on the determined command (step 465).

Figure 4B:
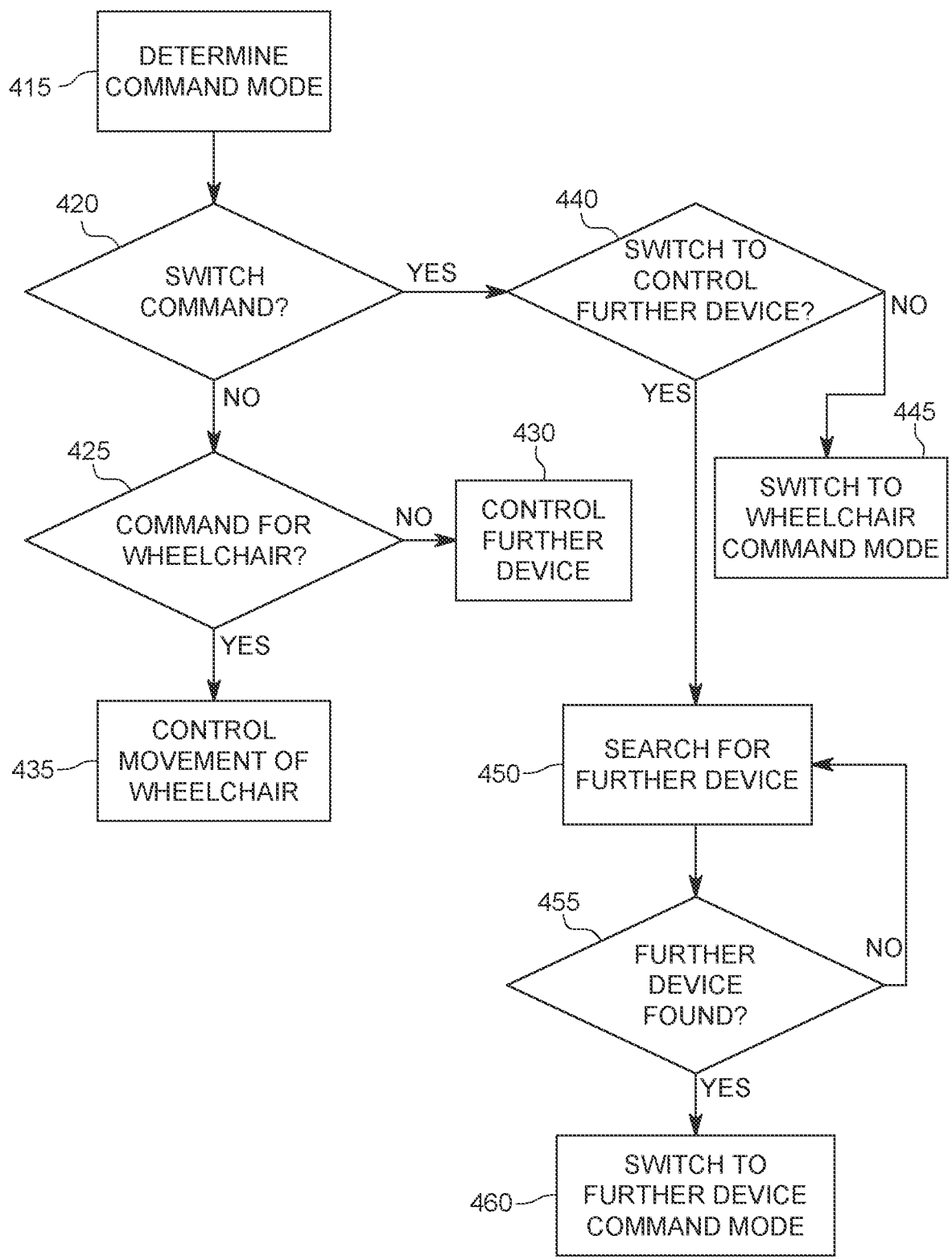

Additional details for how the processor 210 of the power-driven mobility device 205 determines a command corresponding to the received signal will now be described in connection with FIG. 4B. As will be described below, this method involves the use of a switch command for switching between commands directed to movement of the power-driven mobility device 205 and commands for controlling the further device 300, which is a device other than the power-driven mobility device 205. This is particularly advantageous because it allows the use of the same facial movements to send different commands to the power-driven mobility device 205 and device 300, depending upon the control mode.

When the processor 210 of the power-driven mobility device 205 receives a command, it determines whether the command is a switch command (step 420). If the command is not a switch command ("No" path out of decision step 420), the processor 210 determines whether the command is a command for the power-driven mobility device (step 425). This determination is based on which control mode is currently active, the control mode being selected by a switch command and/or being defaulted to controlling the power-driven mobility device 205 or the device 300 upon initial powering on. If the command is not for the power-driven mobility device 205 ("No" path out of decision step 425), then the power-driven mobility device 205 controls the device 300, which is also referred to herein as the further device (step 430). This involves the processor 210 sending the command, determined based upon the signal transmitted from the glasses 105, via wireless communication transmitter 235 (which can be a transceiver), which passes the command to processor 310 for controlling device 320.

If, however, the command is for the power-driven mobility device ("Yes" path out of decision step 425), then the processor 210 of the power-driven mobility device 205 controls movement of the power-driven mobility device 205 (step 435). Again, this involves the processor 210 sending commands to the interface 230, which can include passing the commands through the digital-to-analog converter 240.

Returning to step 420, if the processor 210 determines that the received command is a switch command ("Yes" path out of decision step 420), then the processor 210 determines whether the switch is a switch from controlling the power-driven mobility device 205 to controlling the further device 300 (step 440). If the switch is a switch from controlling the device 300 to controlling the power-driven mobility device 205 ("No" path out of decision step 440), then processor 210 switches to power-driven mobility device command mode (step 445) and interprets any future commands, other than a switch command, as being directed to controlling movement of the power-driven mobility device 205. If the switch is a switch from controlling movement of the power-driven mobility device to controlling the device 300 ("Yes" path out of decision step 440), then the processor 210, using wireless communication transmitter 235, searches for the further device 300 (step 450) and the processor 210 determines whether the further device 300 is found (step 455). If the further device 300 is not found ("No" path out of decision step 455), the processor 210 continues to search for the further device 300 (step 450). A time-out value can be defined, if desired, to revert back to the mode for controlling the power-driven mobility device 205 if the further device 300 is not found at the expiration of the time-out value.

If, however, the processor 210 determines that the further device 300 is found ("Yes" path out of decision step 455), then the processor 210 switches to a mode for controlling the further device 300 (step 460) and interprets any further commands as being used to control the further device 300. It should be recognized that the switch from the mode controlling movement of the power-driven mobility device 205 to controlling the further device 300 does not occur until the further device 300 is found. Thus, any commands that are received prior to this time (i.e., while the processor 210 searches for the further device 300), will be interpreted as commands for controlling movement of the power-driven mobility device 205. It should be recognized, however, that the switch in command modes to controlling the further device 300 can occur immediately in response to receipt of the switch command, if so desired.

The delay in the mode switch from controlling the power-driven mobility device 205 to controlling the further device 300 until the further device 300 is found is particularly advantageous when the power-driven mobility device 205 and further device 300 communicate using line-of-sight communications, such as visible, near-infrared, or infrared frequencies. Specifically, it allows a person to continue to send commands for moving the power-driven mobility device 205 so that the wireless communication transceiver 235 of the power-driven mobility device 205 is aligned with the corresponding wireless communication receiver 305 of the further device 300.

The use of line-of-sight for communicating between the power-driven mobility device 205 and further device 300 is particularly advantageous over the use of radio frequencies because line-of-sight communications do not require the robust initialization of the communication connection typically required by most standardized wireless communication techniques that use radio frequencies. Specifically, the line-of-sight communications do not necessarily involve, but could involve if desired, the initial handshaking between devices, as well as the authorization and authentication signaling required by typical radio frequency communication techniques. In contrast, the power-driven mobility device 205 and the glasses 105 are intended to maintain a long-term connection, and thus the additional time for the initial handshaking between the power-driven mobility device 205 and the glasses 105 is not considered to be as much of a concern as with the communication between the power-driven mobility device 205 and the controlled device 300. Further, because the power-driven mobility device 205 acts as a gateway and can be moved based on commands provided by the glasses 105, the additional authorization and authentication of radio frequency communication techniques ensures that movement of the power-driven mobility device 205 is only performed in response to a person authorized to issue such commands.

Employing the power-driven mobility device 205 as a gateway is also particularly advantageous because a larger processor can be incorporated into the power-driven mobility device 205 without being obtrusive compared to the processor on/in the glasses 105. Further, this reduces the battery consumption of the electronics of the glasses 105, and allows the glasses 105 to operate all of its electronics using a relatively small battery. Thus, the logic for correlating the changes in magnetic fields into commands for controlling the power-driven mobility device 205 and controlled device 300 can be incorporated into the processor 210 of the power-driven mobility device 205. This correlation can be achieved using any number of techniques, including, for example, using a lookup table correlating measured changes in magnetic fields to commands. The disclosed embodiments can employ any communication technique using radio frequencies. However, it is advantageous from a power consumption perspective to employ a short-range radio technology, such as Bluetooth, including Bluetooth Low Energy (BLE), or Wi-Fi.

Now that an overview of the system and method have been presented, additional details of the structure and operation of the system are now presented. Returning to FIG. 1A, in the illustrated embodiment the plurality of magnetic sensors $115_1$-$115_x$ include a magnetic sensor $115_1$ arranged on the bridge of the glasses 105, a magnetic sensor $115_2$ arranged on the lower left portion of the frames (approximately below the left side of the bridge) and a magnetic sensor $115_3$ arranged on the lower right portion of the frames (approximately below the right side of the bridge). An additional magnetic sensor $115_x$ is arranged in the area of one of the hinges of the glasses 105, which is used as a reference sensor to measure external magnetic noise (e.g., the Earth's magnetic field) so that this noise can be canceled from the magnetic fields sensed from the other magnetic sensors $115_1$-$115_3$. Other locations for the additional magnetic sensor $115_x$ is at the bottom-left or bottom-right portions of the glasses 105, or any other portion of the glasses 105 that are as far from the intended location of the magnetic skin tags $103_1$-$130_x$.

Further, as illustrated in FIG. 1B the plurality of magnetic skins tags $130_1$-$130_x$ includes a magnetic skin tag $130_1$ arranged in the glabella of the human face 135, a magnetic skin tag $130_2$ arranged on the left side of the nose of the human face 135, and a magnetic skin tag $130_x$ arranged on the right side of the nose of the human face 135.

Although the magnetic skin tags $130_1$-$130_x$ and magnetic sensors $115_1$-$115_x$ can be arranged in different locations than the arrangement illustrated in FIG. 1B, this particular arrangement was found to be optimal for avoiding accidental activations (i.e., incorrectly interpreting a facial movement as a command), while still allowing for a particularly easy way to send commands. Specifically, it was found that eyebrow and nose movement is less likely accidentally occur than movement of other locations of the face, such as the cheeks, which move when talking and laughing. In order to further reduce accidental activations, in one embodiment commands require movement of both eyebrows in the same direction, a facial movement that is unlikely to occur accidentally. Accidental activations can also be reduced by employing a threshold for the change in magnetic field to qualify as being an intended gesture.

It should be recognized that the magnetic sensors $115_1$-$115_x$ should be arranged in a predefined relationship with respect to the magnetic skin tags $130_1$-$130_x$ in order to properly interpret the change in magnetic fields due to facial movements. In a non-limiting embodiment, the magnetic skin tags $130_1$-$130_x$ are magnetized along the z-axis (which is in the vertical direction when a person's head is level with the earth) and should be arranged either above or below the magnetic sensors $115_1$-$115_x$. Similarly, the magnetic sensors $115_1$-$115_x$ are configured to be sensitive only to changes in magnetic field in the z-axis. Other orientations are possible so long as the magnetic skin tags $130_1$-$130_x$ are magnetized in the direction in which the magnetic skin tags $130_1$-$130_x$ move relative to the magnetic sensors $115_1$-$115_x$ for making the facial expressions that correspond to commands.

Figure 5:
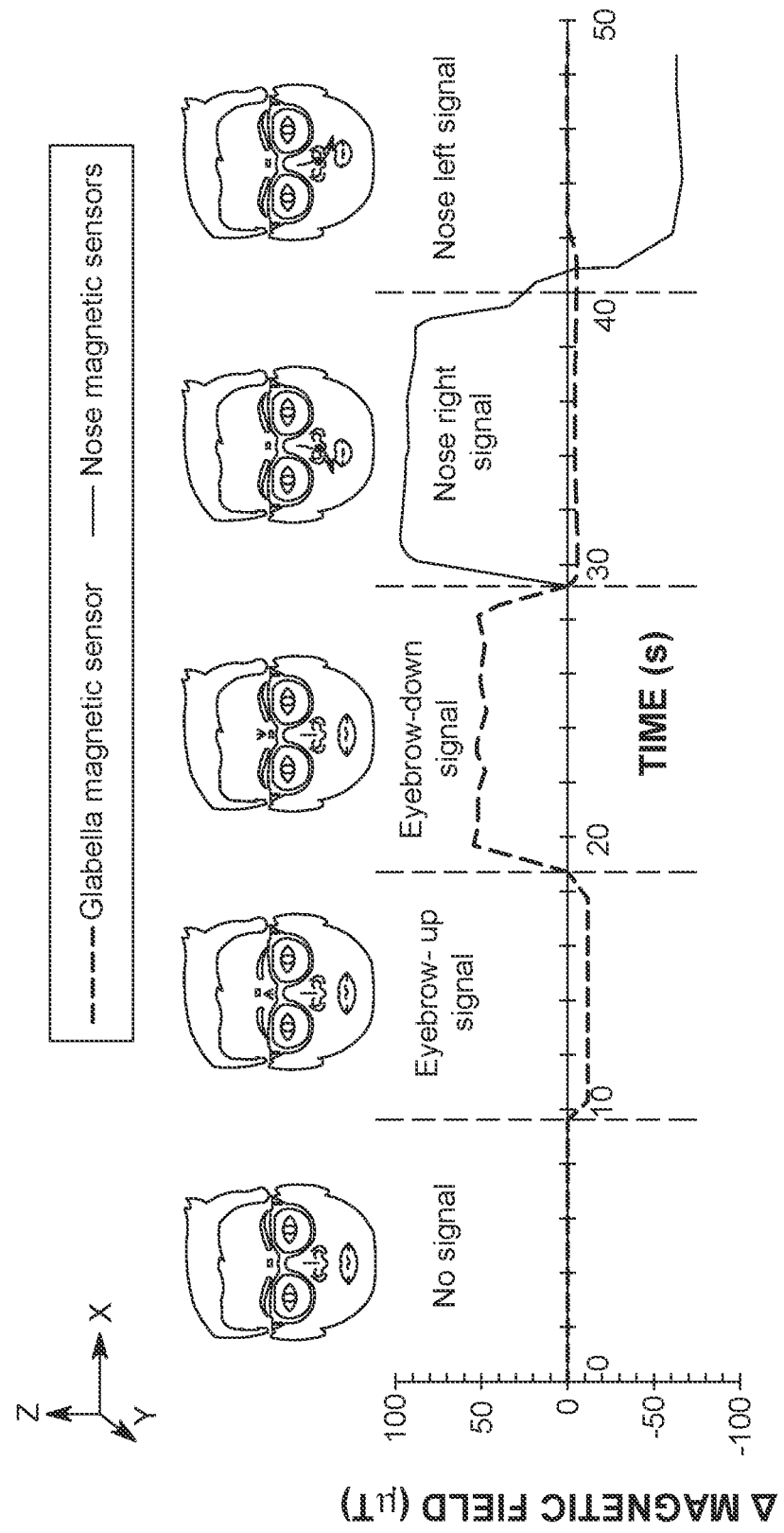
FIG. 5 illustrates the changes in magnetic fields measured by magnetic sensors responsive to moving different portions of a human face.

A non-limiting example of the changes in magnetic field signals for different facial expressions is illustrated in FIG. 5, in which the solid trace represents changes in magnetic fields sensed by the magnetic sensors arranged on the nose and the dashed trace represents changes in magnetic fields sensed by the magnetic sensor on the bridge of the pair of glasses 105. Starting from the left side of the graph, a neutral face is the baseline for measuring changes in magnetic fields, and thus does not produce a change in the magnetic fields sensed by any of the magnetic sensors $115_1$-$115_x$. Moving both eyebrows up causes the magnetic sensor arranged on the bridge of the pair of glasses 105 to sense a negative change in magnetic field and moving both eyebrows down causes the magnetic sensor arranged on the bridge of the pair of glasses 105 to sense a positive change in magnetic field. Moving the nose to the right causes the magnetic sensors arranged on the lower part of the pair of glasses 105 to sense a positive change in magnetic field and moving the nose to the left causes the magnetic sensors arranged on the lower part of the pair of glasses 105 to sense a negative change in magnetic field. In the example illustrated in FIG. 5, the changes in magnetic fields sensed by the magnetic sensors arranged in the lower part of the pair of glasses 105 (i.e., the magnetic sensors arranged to sense nose movements) are differential signals, which improves the signal-to-noise ratio of the signal, and thus reduce false positive and false negative interpretations of facial movements as being intended to issue a command. Specifically, the voltage corresponding to the determined change in magnetic field $V_{nose}$ is the difference between the voltage corresponding to the magnetic field measured for the magnetic skin tag arranged on the right-side of the face $V_R$ and the magnetic skin tag arranged on the left side of the face $V_L$ (i.e., $V_{nose}=V_R-V_L$). Thus, when the nose moves to the right, $V_R$ becomes larger and $V_L$ becomes smaller, and thus $V_{nose}$ is positive. Likewise, when the nose moves to the left, $V_R$ becomes smaller and $V_L$ becomes larger, and thus $V_{nose}$ is negative. It should be recognized that the differential signals can be processed in the opposite manner, i.e., $V_{nose}=V_L-V_R$. As illustrated in FIG. 5, because the magnetic skin tags $130_1$-$130_x$ are magnetized in the direction of the z-axis, the change in magnetic field that is sensed is due to the slight downward movement of the nose when moving the nose left or right.

In addition to commands being based on movement of either the glabella or the nose, a combination of movements can be employed as commands. A non-limiting example of movements (which can also be referred to as gestures) and the corresponding comments is illustrated in the following table:

| Movement | Command |
| --- | --- |
| No expression | Null command (no command issued) |
| Eyebrows up | Move power-driven mobility device forward or turn further device on |
| Eyebrows down | Move power-driven mobility device backward or turn further device off |
| Nose right | Turn power-driven mobility device right or move computer cursor right |
| Nose left | Turn power-driven mobility device left or move computer cursor left |
| Eyebrows up and nose right | Turn power-driven mobility device right while still moving forward or move computer cursor diagonally towards the upper right of the screen |

| Movement | Command |
| --- | --- |
| Eyebrows up and nose left | Turn power-driven mobility device left while still moving forward or move computer cursor diagonally towards the upper left of the screen |
| Eyebrows down and nose right | Turn power-driven mobility device right while still moving backward or move computer cursor diagonally towards the lower right of the screen |
| Eyebrows down and nose left | Turn power-driven mobility device left while still moving backward or move computer cursor diagonally towards the lower left of the screen |
| Double eyebrows up | No command for power-driven mobility device; Select option for further device to further devices that have selection options |
| Triple eyebrows up | Mode switch command between mode for controlling power-driven mobility device and mode for controlling further device |
| Double eyebrows up and nose right | No command for power-driven mobility device; Right-click on computer |
| Double eyebrows up and nose left | No command for power-driven mobility device; Left-click on computer |

The table above, or a similar table, can be implemented as a look-up table by the processor 210 of the power-driven mobility device 205 by including one or more columns for the voltage values provided by each of the magnetic sensors 115$_1$-115$_x$. The correlation between facial movements and commands in the table above is simply one example and other correlations can be employed. Further, double and triple nose movements could be employed to extend the number of available commands.

As discussed above, the plurality of magnetic skins tags 130$_1$-130$_x$ are designed to be attached to a human face, and in many cases are intended to be worn for at least a few hours, if not longer. Thus, the plurality of magnetic skins tags 130$_1$-130$_x$ are designed to be stretchable, flexible, comfortable, and biocompatible. In one non-limiting embodiment, the plurality of magnetic skins tags 130$_1$-130$_x$ are comprised of a mixture of a silicon-based elastomer matrix (e.g., material sold under the name Ecoflex by Smooth-On) with a permanent magnetic powder (e.g., NdFeB) with a 1:1 weight ratio. It was found that this weight ratio offers the best combination of high remanent magnetization and high flexibility. Specifically, this weight ratio produced a magnetic skin tag having a Yong's modulus of 129 kPa, which is more than 17 times lower compared to conventional Sylgard-based magnetic composites, which have a Young's modulus greater than 2,200 kPa. The ultra-low Young's modulus of the magnetic skins tags 130$_1$-130$_x$ makes the presence of the magnetic skin tags almost imperceptible to the wearer. A magnetic skin tag with the 1:1 weight ratio noted above and having dimensions of 10×2×0.07 mm$^3$ exhibited a magnetic flux density of 177 µT at a distance of 7 mm, which provides a sufficient magnetic field for detection by the magnetic sensors with a good signal-to-noise ratio. A magnetic skin tag with the 1:1 weight ratio noted above was subject to stress testing, which demonstrated that the magnetic skin tag maintained its properties over 1000 stress cycles, each cycle involving stretching the magnetic skin tag from its normal length to 180% percent of its normal length and then relaxing the magnetic skin tag to 50% of its normal length. Biocompatibility of the magnetic skin tag with the 1:1 weight ratio noted above was demonstrated using a PrestoBlue cell viability test, where the cells maintained a high viability (i.e., >90%) when cultured on top of the magnetic skin tag for three days.

Because the magnetic skin tags are designed to be worn for extended periods of time, the magnetic skin tags will become uncomfortable unless they are breathable, which can suppress irritations and other feelings of discomfort that might arise from wearing a magnetic skin tag. According to one non-limiting embodiment, breathability is achieved by introducing micro-holes in the magnetic skin tag. For example, after preparing the magnetic skin tag using the 1:1 weight ratio noted above, micro-holes having a diameter of, for example, 70 µm are formed using a 30 W ytterbium fiber laser with a 1.06 µm wavelength. In one embodiment, the magnetic skin tag has a hole density of up to 2,500 holes/cm$^2$, which is four times the density of human sweat glands. Even with the presence of these micro-holes, it was found that a magnetic skin tag that was 0.1 mm thick and had 1,250 holes/cm$^2$ could withstand more than 300% elongation and exhibited a coercivity of 560 mT, which is the required external field to demagnetize the magnetic skin tags. The remanent magnetization is the magnetic field embedded in the magnetic skin tags after being magnetized along the z-axis. In one embodiment, a magnetic skin tag, without any holes, with the 1:1 weight ratio exhibited a remanent magnetization of 126 mT.

Testing showed that the magnetic field drops approximately 20% for every added 1,250 holes/cm$^2$ (or about 1% per 62 holes). Because breathability is characterized by the water vapor transmission rate (WVTR), which is a measure of the vapor permeability of a substrate, the WVTR of the magnetic skin tag with different hole densities were tested and the highest WVTR was found to be 95×10$^3$ g·m$^{-2}$·day$^{-1}$ (with a hole density of approximately 2,500 holes/cm$^2$, which is about two orders of magnitude higher than the range of 200-500 g·m$^{-2}$·day$^{-1}$ of human skin. The WVTR testing also found that a magnetic skin tag with a hole density of 1,250 holes/cm$^2$ offers a high breathability of 60×10$^3$ g·m$^{-2}$·day$^{-1}$ while reducing the magnetic field by only 20% compared to the magnetic field without any holes.

Although embodiments discussed above involve using the processor of the power-driven mobility device as a gateway for sending commands between the glasses and a further device, it should be recognized that further embodiments can omit the power-driven mobility device as a gateway and allow the glasses to send commands directly to a further device. This can be achieved using radio frequency communications and/or line-of-sight communications. When only line-of-sight communications are employed, the glasses can omit the radio frequency transmitter (or transceiver) and include a line-of-sight transmitter (or transceiver), and when only radio frequency communications are employed, the glasses can use the disclosed transmitter (or transceiver) to communicate with the further device using radio frequencies.

As will be appreciated from the discussion above, the disclosed embodiments provide a cost-effective solution for assisting quadriplegics and others with physical disabilities for operating a power-driven mobility device and other devices that does not involve complicated, invasive and bulky equipment, and does not require a large amount of processing power. Accordingly, the disclosed embodiments provide a particularly advantageous system for controlling power-driven mobility devices and other devices.

The disclosed embodiments provide a system for controlling devices, including power-driven mobility devices and devices other than power-driven mobility devices, using facial movements. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A system for controlling at least one device, the system comprising:
   a pair of glasses comprising a glasses frame, wherein a plurality of magnetic sensors, a first processor coupled to the plurality of magnetic sensors, and a wireless communication transmitter coupled to the processor are arranged on or in the glasses frame;
   a plurality of magnetic skins tags arranged on a human face,
   wherein the plurality of magnetic sensors sense movement of at least one of the plurality of magnetic skin tags and transmit a signal corresponding to the sensed movement to the first processor,
   wherein the first processor, responsive to receipt of the signal corresponding to the sensed movement, transmits a switch command to a second processor of a power-driven mobility device for controlling the power-driven mobility device or a further device, via the wireless communication transmitter,
   wherein the switch command, when processed by the second processor of the power-driven mobility device, is configured to switch the controlling from a first control mode of the power-driven mobility device to a second control mode of the further device or vice versa, and
   wherein same facial expressions of the human face are used to send different commands for controlling the power-driven mobility device in the first control mode and the further device in the second control mode.

2. The system of claim 1, wherein the power-driven mobility device comprises:
   a motor operatively coupled to at least one wheel of the power-driven mobility device to control movement of the power-driven mobility device;
   a wireless communication transceiver coupled to the second processor; and
   an interface coupled to the second processor and the motor, wherein the second processor is configured to control movement of the power-driven mobility device based on the signal for controlling the device transmitted to the wireless communication transceiver of the power-driven mobility device.

3. The system of claim 2, wherein the further device comprises a wireless communication receiver, wherein the power-driven mobility device includes a further wireless communication transceiver coupled to the second processor of the power-driven mobility device, and the second processor of the power-driven mobility device is configured to transmit, via the further wireless communication transceiver, a further signal for controlling the further device.

4. The system of claim 3, wherein the wireless communication transceiver of the power-driven mobility device and the wireless communication transmitter of the pair of glasses operate using radio frequencies, and wherein the further wireless communication transceiver and the wireless communication transceiver of the device operate using line-of-sight communications.

5. The system of claim 1, wherein
   the further device is a device other than the power-driven mobility device,
   the power-driven mobility device comprises
      a wireless communication transceiver coupled to the second processor of the power-driven mobility device, the wireless communication transceiver configured to communicate with the wireless communication transmitter of the pair of glasses, and
      a further wireless communication transmitter coupled to the second processor of the power-driven mobility device, wherein the further wireless communication transmitter is configured to transmit, to the further device, a signal for controlling the further device.

6. The system of claim 5, wherein the further device is a light, a door, a window, an elevator, a television, a set-top box, a pedestrian traffic light, a phone, curtains, doors, or a computer.

7. The system of claim 1, wherein
   the plurality of magnetic skin tags comprise first and second magnetic skin tags arranged on opposite sides of a nose of the human face, and a third magnetic skin tag arranged on a forehead of the human face, and
   the plurality of magnetic sensors of the pair of glasses include a first magnetic sensor arranged on a bridge of the pair of glasses, and a second and third magnetic sensor arranged on opposite rims of the pair of glasses.

8. The system of claim 7, wherein the plurality of magnetic sensors comprise a fourth magnetic sensor, which is arranged next to a hinge of the pair of glasses, in a bottom-left portion of the pair of glasses, or in a bottom-right portion of the pair of glasses, wherein the fourth magnetic sensor is a reference sensor.

9. The system of claim 1, wherein the plurality of magnetic skin tags are comprised of a mixture, in equal parts, of a silicon-based elastomer matrix and a magnetic powder.

10. The system of claim 9, wherein each of the plurality of magnetic skin tags include a plurality of perforations configured to allow skin of the human face covered by the magnetic skin tags to pass water vapor through the respective one of the plurality of magnetic skin tags.

11. A method for controlling at least one device, the method comprising:
    sensing, by at least one of a plurality of magnetic sensors arranged on a glasses frame, a change in a magnetic field due to movement of at least one of a plurality of magnetic skin tags arranged on a human face;
    transmitting, by a wireless communication transmitter coupled to or arranged in the glasses frame, a switch command, corresponding to the sensed change in the magnetic field, to a processor of a power-driven mobility device via a wireless communication transceiver of the power-driven mobility device;
    determining, by the processor of the power-driven mobility device, whether the switch command is for controlling the power-driven mobility device during a first control mode or for controlling a further device during a second control mode; and controlling, by the processor of the power-driven mobility device, in response to same facial expressions of the human face, the power-driven mobility device in the first control mode or the further device in the second control mode.

12. The method of claim 11, further comprising:

receiving a movement command for moving the power-driven mobility device, the controlling of the power-driven mobility device based on the movement command comprises sending, by the processor of the power-driven mobility device, a signal to an interface of the power-driven mobility device, and the interface of the power-driven mobility device is coupled to a motor of the power-driven mobility device and is configured to control movement of the power-driven mobility device using the motor.

13. The method of claim 11, further comprising:

receiving a control command for controlling the further device, the controlling of the further device based on the control command by the processor of the power-driven mobility device comprises sending, via a further wireless transmitter of the power-driven mobility device, the control command to the further device using line-of-sight communications.

14. The method of claim 13, further comprising:

receiving, by the processor of the power-driven mobility device from the wireless communication transmitter coupled to or arranged in the glasses frame, the switch command prior to receiving the command corresponding to the signal;

searching, responsive to receipt of the switch command, for the further device, which is a device other than the power-driven mobility device; and transmitting, by the processor of the power-driven mobility device, additional commands to the further device once the further device is located, wherein signals corresponding to commands that are received by the processor of the power-driven mobility device prior to locating the further device are used to control movement of the power-driven mobility device.

15. The method of claim 11, wherein the sensed change in magnetic field is due to a movement of at least one eyebrow or a nose of the human face.

16. A system for controlling a power-driven mobility device and at least one device, the system comprising:

a pair of glasses comprising a glasses frame, a plurality of magnetic sensors, a first processor coupled to the plurality of magnetic sensors, and a wireless communication transmitter coupled to the processor;

a plurality of magnetic skins tags arranged on a human face, wherein the plurality of magnetic sensors are configured to sense movement of at least one of the plurality of magnetic skin tags and transmit a signal corresponding to the sensed movement to the processor; and a power-driven mobility device comprising a motor, a second processor, an interface coupled to the second processor and motor, a wireless communication transceiver coupled to the second processor, and a wireless communication transmitter coupled to the second processor, wherein the first processor of the pair of glasses, responsive to receipt of the signal corresponding to the sensed movement, transmits a switch command, for controlling the power-driven mobility device or the at least one device, to the second processor of the power-driven mobility device, wherein the at least one device comprises a wireless receiver configured to wirelessly communicate with the wireless communication transmitter of the power-driven mobility device, wherein the switch command, when processed by the second processor of the power-driven mobility device, configures the second processor of the power-driven mobility device to switch the controlling from a first control mode of the power-driven mobility device to a second control mode of the at least one device or vice versa, and wherein same facial expressions of the human face are used to send different commands for controlling the power-driven mobility device in the first control mode and the at least one device in the second control mode.

17. The system of claim 16, wherein the wireless communication transmitter of the pair of glasses and the wireless communication transceiver of the power-driven mobility device communicate using a first communication technique, and wherein the wireless communication transmitter of the power-driven mobility device and the wireless communication receiver of the at least one device communicate using a second communication technique.

18. The system of claim 16, wherein the first communication technique uses radio frequencies and the second communication technique uses line-of-sight communications.

19. The system of claim 16, wherein the at least one device is a light, a door, a window, an elevator, a television, a pedestrian traffic light, a phone, curtains, doors, or a computer.

20. The system of claim 16, wherein the plurality of magnetic skin tags comprise first and second magnetic skin tags arranged on opposite sides of a nose of the human face, and a third magnetic skin tag arranged on a forehead of the human face, and the plurality of magnetic sensors of the pair of glasses include a first magnetic sensor arranged on a bridge of the pair of glasses, and a second and third magnetic sensor arranged on opposite rims of the pair of glasses.

* * * * *